(12) United States Patent
Shirakawa et al.

(10) Patent No.: US 9,465,035 B2
(45) Date of Patent: Oct. 11, 2016

(54) NANODIAMOND PARTICLE AND METHOD OF MANUFACTURING THE SAME, AND FLUORESCENT MOLECULAR PROBE AND METHOD OF ANALYZING STRUCTURE OF PROTEIN

(71) Applicant: JAPAN SCIENCE AND TECHNOLOGY AGENCY, Kawaguchi-shi, Saitama (JP)

(72) Inventors: Masahiro Shirakawa, Kyoto (JP); Shingo Sotoma, Kyoto (JP); Ryuji Igarashi, Kyoto (JP); Yoshie Harada, Kyoto (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 14/434,640

(22) PCT Filed: Oct. 10, 2013

(86) PCT No.: PCT/JP2013/077591
§ 371 (c)(1),
(2) Date: Apr. 9, 2015

(87) PCT Pub. No.: WO2014/058012
PCT Pub. Date: Apr. 17, 2014

(65) Prior Publication Data
US 2015/0276754 A1   Oct. 1, 2015

(30) Foreign Application Priority Data
Oct. 12, 2012 (JP) ................................. 2012-226721

(51) Int. Cl.
*C01B 31/06* (2006.01)
*G01N 33/68* (2006.01)
(Continued)

(52) U.S. Cl.
CPC ........... *G01N 33/6803* (2013.01); *C01B 31/06* (2013.01); *C01B 31/065* (2013.01);
(Continued)

(58) Field of Classification Search
CPC ... C01B 31/06; C01B 31/065; G01R 33/323; G01R 33/60; G01N 2021/6439; G01N 21/6428; G01N 24/00; G01N 24/10; G01N 24/087; G01N 33/582; G01N 33/68; G01N 33/6803; Y10T 436/203332; Y10T 436/23; Y10T 436/24
USPC ......... 436/86, 127, 131, 164, 172, 173, 145; 423/416, 579; 568/817
See application file for complete search history.

(56) References Cited

U.S. PATENT DOCUMENTS
2015/0192596 A1* 7/2015 Englund .............. G01N 21/643
436/163

FOREIGN PATENT DOCUMENTS
CN 102432003 A 5/2012
CN 102725833 A 10/2012
(Continued)

OTHER PUBLICATIONS

Kratochvilova et al. Physica Status Solidi A, vol. 207, No. 9, 2010, pp. 2045-2048.*
Fu et al., "Characterization and Application of Single Fluorescent Nanodiamonds as Cellular Biomarkers," *Proc. Natl. Acad. of Sci. U.S.A.*, 104(3): 727-732 (Jan. 16, 2007).
Petrakova et al., "Luminescence of Nanodiamond Driven by Atomic Functionalization: Towards Novel Detection Principles," *Advanced Functional Materials*, 22(4): 812-819 (Feb. 22, 2012).
(Continued)

*Primary Examiner* — Maureen Wallenhorst
(74) *Attorney, Agent, or Firm* — Leydig, Voit & Mayer, Ltd.

(57) ABSTRACT

A nanodiamond particle including an NV center having ODMR intensity enhanced, of which surface is modified with a functional group containing a heteroatom, is provided. This nanodiamond particle as being chemically modified can serve for a fluorescent molecular probe which can be made use of in a biological system. By tracking a rotational motion of the NV center included in this fluorescent molecular probe, structural change of a protein can be analyzed in real time. The functional group containing a heteroatom can be at least any functional group of a hydroxyl group and a hydroxyalkyl group, or a carboxyl group.

11 Claims, 14 Drawing Sheets

(51) Int. Cl.
- *G01N 24/10* (2006.01)
- *G01N 33/58* (2006.01)
- *G01R 33/32* (2006.01)
- *G01R 33/60* (2006.01)
- G01N 21/64 (2006.01)
- G01N 24/08 (2006.01)

(52) U.S. Cl.
CPC .......... *G01N 24/10* (2013.01); *G01N 33/582* (2013.01); *G01R 33/323* (2013.01); *G01R 33/60* (2013.01); G01N 21/6428 (2013.01); G01N 24/087 (2013.01); G01N 2021/6439 (2013.01); *Y10T 436/203332* (2015.01); *Y10T 436/23* (2015.01); *Y10T 436/24* (2015.01)

(56) References Cited

FOREIGN PATENT DOCUMENTS

| | | |
|---|---|---|
| JP | H04-295782 A | 10/1992 |
| JP | 2011-180570 A | 9/2011 |
| JP | 2012-121748 A | 6/2012 |
| WO | WO 2011/060143 A1 | 5/2011 |

OTHER PUBLICATIONS

Japanese Patent Office, International Search Report in International Patent Application No. PCT/JP2013/077591 (Nov. 19, 2013).

Chinese Patent Office, The First Office Action in Chinese Patent Application No. 2013800649434 (Feb. 25, 2016).

Krueger et al., "Surface functionalization of detonation diamond suitable for biological applications," *Journal of Materials Chemistry*, 16(24): 2322-2328 (Jan. 1, 2006).

Krueger et al., "Functionality if Key: Recent Progress in the Surface Modification of Nanodiamond," *Advanced Functional Materials*, 22(5): 890-906 (Mar. 7, 2012).

Zhao et al., "Chromatographic Separation of Highly Soluble Diamond Nanoparticles Prepared by Polyglycerol Grafting," *Angewandte Chemie International Edition*, 50(6): 1388-1392 (Jan. 18, 2011).

European Patent Office, Extended European Search Report in European Patent Application No. 13844813.9 (Jun. 1, 2016).

Japanese Patent Office, Notice of Grounds of Rejection in Japanese Patent Application No. 2014-540890 (Jun. 7, 2016) English translation.

* cited by examiner

NANODIAMOND PARTICLE AND METHOD OF MANUFACTURING THE SAME, AND FLUORESCENT MOLECULAR PROBE AND METHOD OF ANALYZING STRUCTURE OF PROTEIN

CROSS-REFERENCE TO RELATED APPLICATIONS

This patent application is the U.S. national phase of International Patent Application No. PCT/JP2013/077591, filed Oct. 10, 2013, which claims the benefit of Japanese Patent Application No. 2012-226721, filed on Oct. 12, 2012, which are incorporated by reference in their entireties herein.

TECHNICAL FIELD

The present invention relates to a nanodiamond particle and a method of manufacturing the same as well as a fluorescent molecular probe and a method of analyzing a structure of a protein.

BACKGROUND ART

Various fluorescent molecular probes used for analysis of a structure of a protein or a structure or a function of biomolecules such as a protein have been known. For example, the fluorescent molecular probe can be exemplified by fluorescamine specifically reacting with a primary amine and exhibiting fluorescence. Then, various types of information on a molecular structure such as a motion or an orientation of a target protein can be collected by labeling a target protein with the fluorescent molecular probe and observing the target protein with a fluorescence microscope. A nanodiamond particle has recently attracted attention as a fluorescent substance used for such a fluorescent molecular probe (for example, Japanese Patent Laying-Open No. 2011-180570 (PTD 1)).

CITATION LIST

Patent Document

PTD 1: Japanese Patent Laying-Open No. 2011-180570

SUMMARY OF INVENTION

Technical Problem

A protein is deeply involved with a life phenomenon in a biological system. Tracking structural change of a protein in a biological system is extremely important in clarifying a function of the protein and clarifying a mechanism of expression or development of diseases. A structure of a protein has conventionally been analyzed exclusively "in-vitro", that is, in a test tube. An environment around a protein, however, is significantly different between a biological system "in-vivo" where a protein actually functions and a test tube. Therefore, a situation where a result of observation in the test tube is applicable as it is to a structure or a function of the biological system is limited, and early establishment of a method of analyzing a structure of a protein in a biological system has been desired.

Conventionally, for analyzing a structure of a protein, a method of analyzing a molecular structure with nuclear magnetic resonance [hereinafter also denoted as "NMR"] or a fluorescent molecule observation method with the use of a fluorescence microscope has mainly been employed.

Since NMR is capable of non-invasive measurement and has a high spatial resolution at an atomic level, a large amount of information on a steric structure can be collected. In contrast, NMR is low in sensitivity and also in time resolution, and hence it has been difficult to conduct real-time observation.

The fluorescent molecule observation method is capable of single-molecule measurement and also real-time observation and measurement. In contrast, the fluorescent molecule observation method has been low in spatial resolution, and it has extremely been difficult to measure what is called structural fluctuations and structural change. Furthermore, in many cases, a fluorescent substance used for a fluorescent molecular probe has been toxic, which has made the fluorescent molecule observation method unsuitable for non-invasive measurement.

Thus, with existing methods, it has been impossible to non-invasively observe change in structure of a single molecule of a protein in a biological system in real time.

An optically-detected magnetic resonance method [hereinafter also denoted as an "ODMR method"] has been known as means allowing detection of magnetic resonance of a sample with high sensitivity. With the ODMR method, magnetic resonance is detected with high sensitivity by simultaneously emitting excitation light and applying high-frequency magnetic field to a sample and sensing change in amount of emission of fluorescence. Such measurement means is hereinafter also denoted herein as ODMR measurement.

For example, studies about application of the ODMR method, in which the magnetic resonance method and the fluorescent molecule observation method are combined, to analysis of a structure of a protein in a biological system as with a fluorescence microscope apparatus described in PTD 1 have recently been conducted. The studies show possibility of a nanodiamond particle as a fluorescent molecular probe.

A nanodiamond particle including a defect complex consisting of a nitrogen atom and a vacancy (hereinafter also denoted as an "NV center") in a diamond crystal has been known to emit fluorescence at the NV center and vary an amount of emission of fluorescence with magnetic resonance. Here, the NV center refers to a defect complex consisting of a nitrogen atom 2 (N) having replaced a carbon atom 1 in a diamond crystal and a vacancy 3 (V) adjacent to nitrogen atom 2, as shown in FIG. 1.

Fluorescence at the NV center is less in bleaching or blinking of fluorescence and highly adaptive to fluorescence analysis. Since the nanodiamond particle is a substance composed of carbon atoms, it is considered to extremely be low in toxicity to a biological system, and a surface of the particle is readily chemically modified for labeling a target protein. Therefore, the nanodiamond particle is viable as a fluorescent molecular probe to be used in a biological system.

When ODMR measurement of the nanodiamond particle including the NV center as above is conducted and results are displayed on a two-dimensional coordinate having an amount of emission of fluorescence represented on the ordinate and a frequency of magnetic field represented on the abscissa, a downward peak of emission of fluorescence is observed in specific high-frequency magnetic field. Here, a spectrum displayed on the two-dimensional coordinate is herein also denoted as an "ODMR spectrum" and the downward peak is also denoted as an "ODMR signal".

In ODMR measurement, a rate of decrease in amount of emission of fluorescence calculated in an equation (I) below is defined as "ODMR intensity" where L(ON) represents an amount of light emission at the time when high-frequency magnetic field is applied and L(OFF) represents an amount of light emission at the time when magnetic field is not applied.

$$(\text{ODMR intensity})=1-\{L(ON)/L(OFF)\} \quad (I)$$

The downward peak (the ODMR signal) splits at the NV center placed in static external magnetic field, and splitting of the peak varies with a rotational motion of the NV center. Therefore, precise and real-time analysis of a structure of a protein in a biological system which has not been achieved by the existing methods above may be realized by employing the nanodiamond particle including the NV center as a fluorescent molecular probe, labeling a target protein with the fluorescent molecular probe, and measuring an ODMR spectrum.

Here, in order to realize the method of analyzing a structure of a protein in a biological system as above, a nanodiamond particle including an NV center having extremely high ODMR intensity is required.

Currently, however, ODMR intensity of a nanodiamond particle including an NV center is not sufficient for stable measurement within a biological system, and a method of analyzing a structure of a protein as above has not yet been established. A method of enhancing ODMR intensity of a nanodiamond particle including an NV center has not so far been reported.

The present invention was made in view of such circumstances, and an object thereof is to provide a nanodiamond particle including an NV center having ODMR intensity enhanced, and a novel method of analyzing a structure of a protein by employing a fluorescent molecular probe obtained by chemically modifying the nanodiamond particle.

Solution to Problem

A nanodiamond particle according to the present invention has ODMR intensity of an NV center present in the particle enhanced as a surface of the particle is modified with a specific functional group.

Namely, a nanodiamond particle according to the present invention is characterized by including an NV center having ODMR intensity enhanced, with the surface thereof being modified with a functional group containing a heteroatom.

Here, the functional group containing the heteroatom is preferably an electron-donating functional group. The functional group containing the heteroatom is preferably at least any of a hydroxyl group and a hydroxyalkyl group. The functional group containing the heteroatom may be a carboxyl group.

The nanodiamond particle preferably has an average particle size not smaller than 1 nm and not greater than 50 nm.

The ODMR intensity represents a rate of decrease in amount of emission of fluorescence originating from excitation light when high-frequency magnetic field from 1 to 5 GHz is applied.

A specific form of use of the nanodiamond particle according to the present invention can be exemplified by a powdery reagent formed from the nanodiamond particle or a reagent obtained by dispersing the nanodiamond particle in a liquid.

Furthermore, the present invention also relates to a method of manufacturing the nanodiamond particle above, and the manufacturing method is a method of manufacturing a nanodiamond particle having ODMR intensity enhanced, which includes the steps of preparing a nanodiamond particle and performing treatment for selectively enhancing a ratio of modification with one or more types of functional groups containing a heteroatom, of functional groups present at a surface of the nanodiamond particle.

Here, preferably, one or more types of the functional groups containing the heteroatom are a hydroxyl group and/or a hydroxyalkyl group (at least any of a hydroxyl group and a hydroxyalkyl group) and the step of performing treatment is the step of performing reduction treatment.

One or more types of the functional groups containing the heteroatom may be a carboxyl group and the step of performing treatment may be the step of performing oxidation treatment.

The present invention also relates to a fluorescent molecular probe including the nanodiamond particle above, and the fluorescent molecular probe is characterized by being obtained by chemically modifying the nanodiamond particle including an NV center having ODMR intensity enhanced. This fluorescent molecular probe can be made use of, for example, as a powdery reagent or a reagent dispersed in a liquid.

Furthermore, the present invention also relates to a method of analyzing a structure of a protein, and the method of analyzing a structure is a method of analyzing a structure of a protein for sensing structural change of a target protein by emitting excitation light and applying high-frequency magnetic field from 1 to 5 GHz to the target protein labeled with the fluorescent molecular probe and sensing a peak magnetic field frequency at which an amount of emission of fluorescence decreases. Namely, the method of analyzing a structure includes the steps of labeling a target protein with the fluorescent molecular probe and sensing structural change of the target protein by emitting excitation light and applying high-frequency magnetic field from 1 to 5 GHz to the labeled target protein and sensing a peak magnetic field frequency at which an amount of emission of fluorescence decreases.

Here, the peak magnetic field frequency splits under static external magnetic field, and a rotational motion of an NV center included in the fluorescent molecular probe can be sensed based on magnitude of splitting of the peak magnetic field frequency.

Advantageous Effects of Invention

The nanodiamond particle according to the present invention exhibits extremely high ODMR intensity. Therefore, it can be made use of as a fluorescent molecular probe in a biological system, and precise and real-time analysis of a structure of a protein in a biological system may be realized by employing the fluorescent molecular probe.

DESCRIPTION OF EMBODIMENTS

First Embodiment

Though an embodiment of the present invention (hereinafter also denoted as the "present embodiment") will be described hereinafter in further detail, the present invention is not limited thereto.

<Nanodiamond Particle Including NV Center Having ODMR Intensity Enhanced>

A nanodiamond particle in the present embodiment will be described below. The nanodiamond particle in the present embodiment has a surface modified with a functional group containing a heteroatom and includes an NV center having ODMR enhanced.

<<Nanodiamond Powders>>

A method of manufacturing nanodiamond powders serving as a source material is not particularly restricted, and they may be manufactured with any method. A method of manufacturing nanodiamond powders can be exemplified by a chemical vapor deposition (CVD) method, a detonation method, and a high pressure high temperature method (an HPHT method).

One of objects of the nanodiamond particle in the present embodiment is use for a method of analyzing a structure of a protein in a biological system. Since nanodiamond powders obtained with the CVD method and the HPHT method generally have wide particle size distribution, particle size distribution is preferably adjusted by making classification as appropriate. Here, for example, ultracentrifugation or size exclusion chromatography can suitably be employed as a classification method. On the other hand, nanodiamond powders obtained with the detonation method could be employed as they are, without performing a classification operation, because, with the detonation method, based on principles of the manufacturing method, large particles are not formed but powders uniform in particle size approximately from 4 to 5 nm are obtained.

In consideration of use in a biological system, a nanodiamond particle has an average particle size preferably as small as possible, and the nanodiamond particle has an average particle size preferably not greater than 50 nm, more preferably not greater than 40 nm, and most preferably not greater than 30 nm. When an average particle size exceeds 50 nm, dispersibility tends to lower, which is not preferred. Though an average particle size is preferably as small as possible as described above, from a point of view of having an NV center and securing high crystallinity, the average particle size is preferably not smaller than 1 nm. As described previously, nanodiamond powders obtained with the detonation method can have a range of particle size approximately from 4 to 5 nm. Therefore, nanodiamond powders obtained with the detonation method are particularly suitable as a source material for the nanodiamond particle in the present embodiment. An "average particle size" can be measured, for example, with a dynamic light scattering method or a laser diffraction method.

<<NV Center>>

Figure 1:
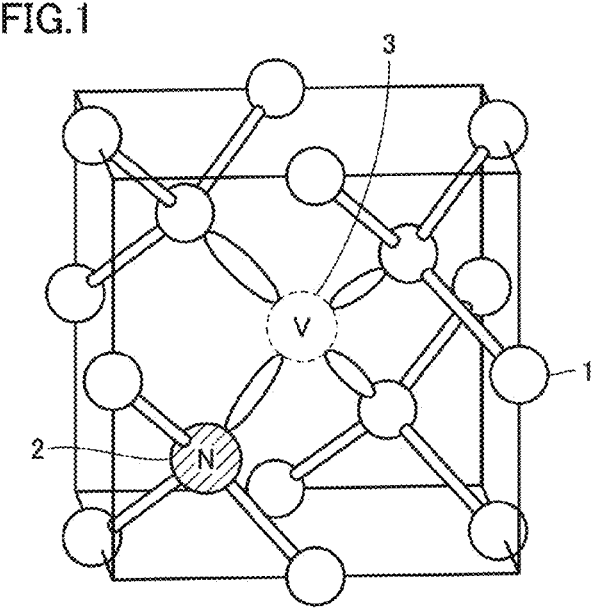
FIG. 1 is a schematic conceptual diagram of an NV center in a diamond crystal.

A nanodiamond particle in the present embodiment includes an NV center having ODMR intensity enhanced. Here, the NV center refers to a defect complex consisting of nitrogen atom 2 having replaced carbon atom 1 in a diamond crystal and a vacancy 3 adjacent to nitrogen atom 2, as shown in FIG. 1.

<<Formation of NV Center>>

Figure 2:
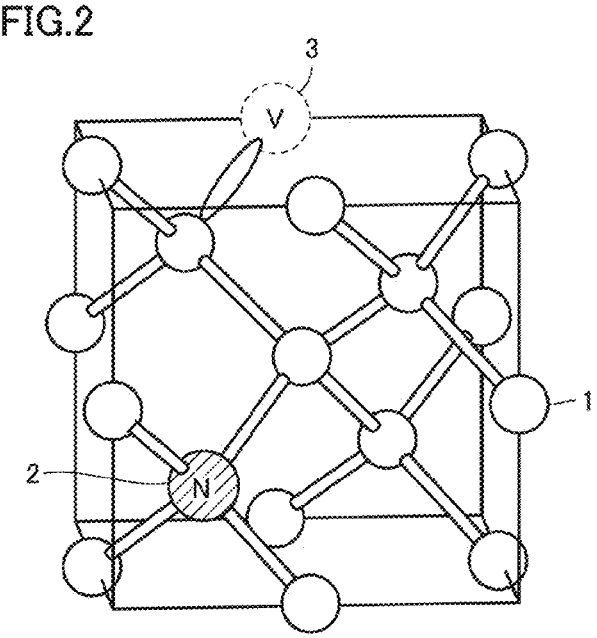
FIG. 2 is a schematic conceptual diagram showing one example of arrangement of a nitrogen atom and a vacancy in a diamond crystal.

In general, when nanodiamond powders are manufactured with the method as above, nitrogen atoms have been introduced as an impurity into a diamond crystal, and simultaneously, a vacancy resulting from a missing carbon atom is also present. With such a state, however, for example, as shown in FIG. 2, nitrogen atom 2 and vacancy 3 do not form an adjacent pair and do not constitute an NV center.

<<Heat Treatment in Vacuum>>

Then, nitrogen atom 2 and vacancy 3 can be bonded to each other by subjecting nanodiamond powders to heat treatment in vacuum at a high temperature from 700° C. to 1000° C. Thus, the NV center shown in FIG. 1 is formed in a diamond crystal.

<<Heat Treatment in Air>>

When heat treatment in vacuum at a high temperature is carried out as above, however, a part of a diamond structure at a surface of a particle is graphitized. When the surface is thus covered with graphite, the nanodiamond particle does not exhibit good emission of fluorescence even though it has an NV center in the inside of the crystal.

Then, in order to obtain a nanodiamond particle exhibiting good emission of fluorescence, it is necessary to oxidize the surface by carrying out further heat treatment in air from 400° C. to 600° C. after heat treatment in vacuum.

<<NV (−) and NV (0)>>

When the nanodiamond particle having an NV center formed in the inside of the diamond crystal as above is irradiated with excitation light, it emits fluorescence. Then, when excitation light is emitted and simultaneously high-frequency magnetic field is applied to the diamond particle to thereby generate electron spin resonance [hereinafter also denoted as "ESR"], an amount of emission of fluorescence may decrease.

This phenomenon is caused by presence of NV (−) among NV centers, which forms a spin state in which no fluorescence is emitted at the time when ESR occurs. The phenomenon will be described below with reference to FIGS. 3 to 8.

Figure 3:
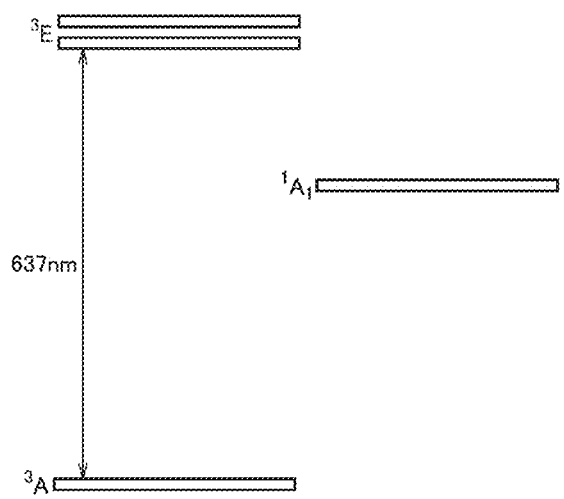
FIG. 3 is a conceptual diagram showing one example of an energy level of an NV center.

As shown in FIG. 3, a ground level of the NV center is expressed as a spin-triplet ($^3A$) and an excitation state is expressed as a spin-triplet ($^3E$). There is an energy gap corresponding to a wavelength of 637 nm between ($^3A$) and ($^3E$). In addition, there is a spin-singlet ($^1A_1$) between ($^3A$) and ($^3E$).

Figure 4:
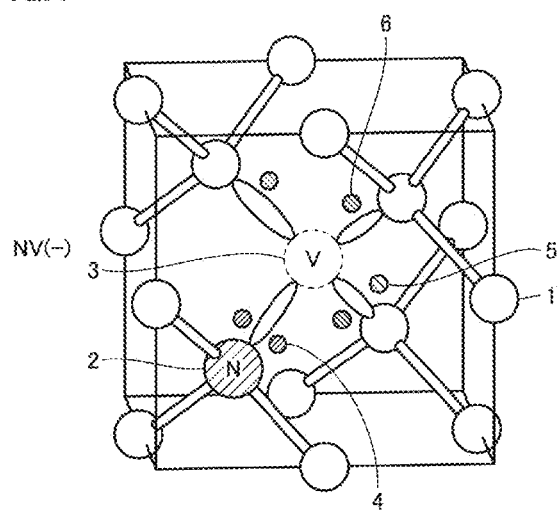
FIG. 4 is a schematic conceptual diagram showing NV (−) in a diamond crystal.

As shown in FIG. 4, NV (−) has acquired an extra electron 5 for vacancy 3 adjacent to nitrogen atom 2. Presence of this electron leads to two unpaired electrons 6, and a spin level of S=1 can be formed.

Figure 6:
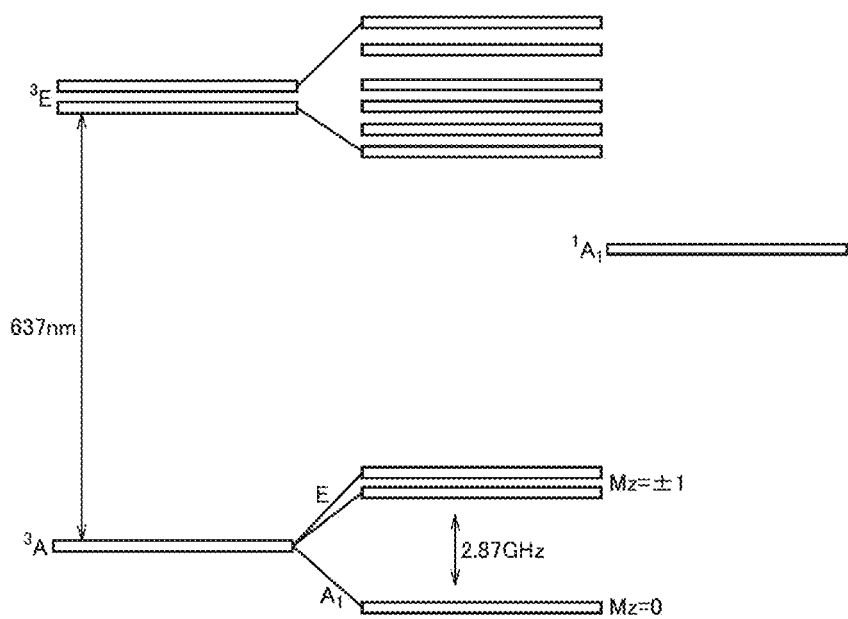
FIG. 6 is a schematic conceptual diagram showing one example of an energy level of NV (−).

Therefore, as shown in FIG. 6, at NV (−), the ground level splits into a ground level ($A_1$) of Mz=0 and a sublevel (E) of Mz=±1, the splitting having an energy gap corresponding to approximately 2.87 GHz, even without application of static magnetic field. Therefore, when high-frequency magnetic field of approximately 2.87 GHz is applied, ESR occurs even in a zero magnetic field environment.

Figure 7:
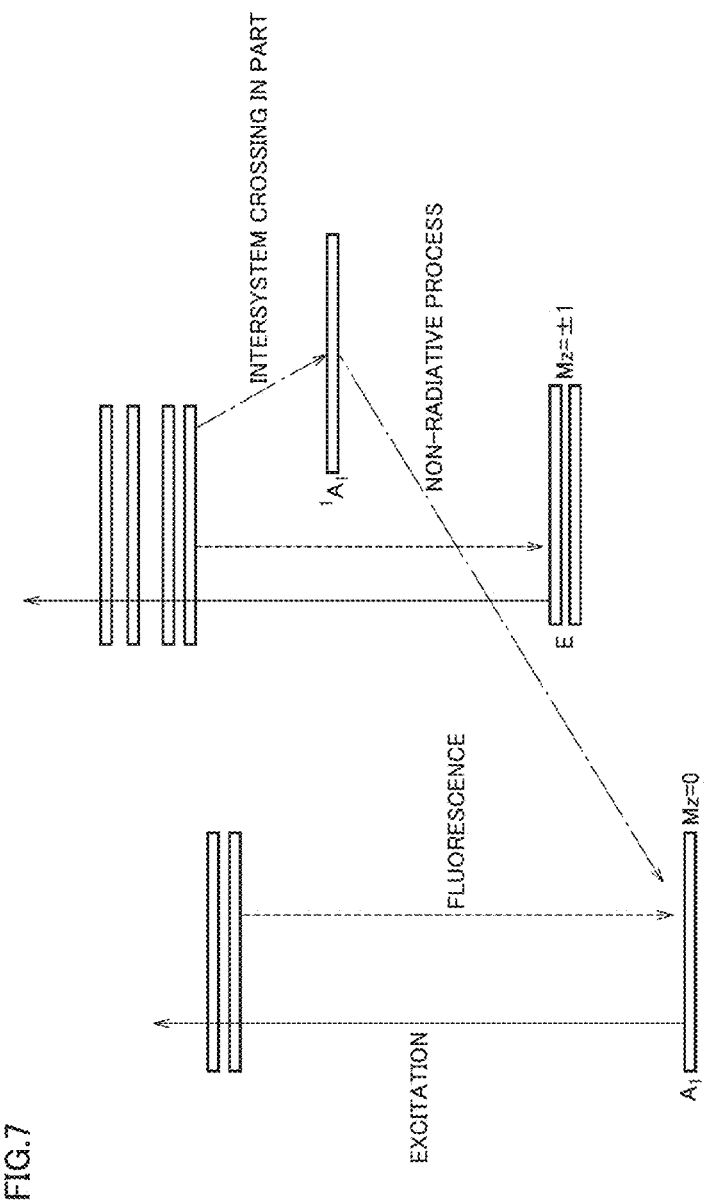
FIG. 7 is a schematic conceptual diagram showing one example of an energy level when NV (−) emits fluorescence.
Figure 8:
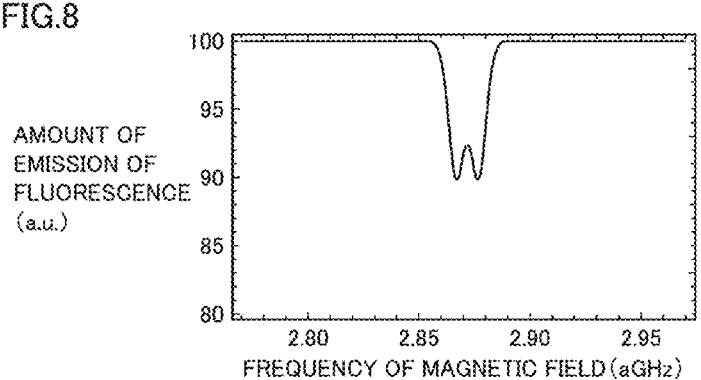
FIG. 8 is a diagram showing one example of an ODMR spectrum according to an embodiment of the present invention.

Here, FIG. 7 shows a process of relaxation at the time when excitation light is emitted while ESR occurs at NV (−). Some of electrons excited from the sublevel (E) of Mz=±1 by excitation light experience intersystem crossing, and go through the spin-singlet ($^1A_1$) and a non-radiative process in which no fluorescence is emitted, as shown with a chain dotted line in FIG. 7. Namely, this is observed as decrease in amount of emission of fluorescence (an ODMR signal) as shown in FIG. 8. As more electrons go through the non-radiative process, the ODMR signal is higher (in other words, ODMR intensity is enhanced).

Figure 5:
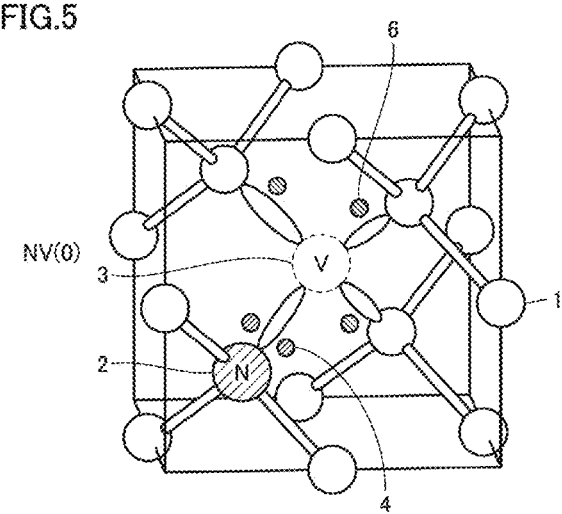
FIG. 5 is a schematic conceptual diagram showing NV (0) in a diamond crystal.

At NV (0), on the other hand, there is no extra electron 5 at the NV center as shown in FIG. 5, and hence a spin level of S=1/2 is set. Therefore, at NV (0), even though excitation light is emitted, transition between ($^3A$) and ($^3E$) shown in FIG. 3 only occurs and the non-radiative process is not experienced. Namely, no ODMR signal is exhibited (ODMR inactive).

As can be seen from the description above, if an occurrence of NV (−) among NV centers can be increased, ODMR intensity can be enhanced.

The present inventors have conducted dedicated studies about a method of enhancing an occurrence of NV (−) in a nanodiamond particle including an NV center, and consequently, found that an occurrence of NV (−) can be increased and ODMR intensity can drastically be enhanced by modifying a surface of a nanodiamond particle with a specific functional group and completed the present invention.

Namely, the nanodiamond particle in the present embodiment is a nanodiamond particle in which an NV center has ODMR intensity enhanced by modification of a surface with a functional group containing a heteroatom.

<<Functional Group Containing Heteroatom>>

A heteroatom herein refers to an atom other than carbon (C) and hydrogen (H), and to an atom having a lone pair on the atom in a functional group. Such a heteroatom can be exemplified by oxygen (O), nitrogen (N), and sulfur (S). A functional group containing a heteroatom can be exemplified by a hydroxyl group (—OH), a hydroxyalkyl group (—CH$_2$OH, —ROH: R representing an alkyl group), a carboxyl group (—COOH), an amino group (—NH$_2$), an alkyl amino group (—NHR, —NR$_2$: R representing an alkyl group), and a thiol group (—SH).

<<Electron Donating Property>>

The functional group containing a heteroatom is preferably an electron-donating functional group. Here, "electron-donating" herein means an electron donating property owing to a resonance effect of a lone pair on a heteroatom.

By modifying a surface of a nanodiamond particle with an electron-donating functional group containing a heteroatom, formation of NV (−) can be promoted.

A hydroxyl group, a hydroxyalkyl group, and a carboxyl group among the functional groups containing a heteroatom above tend to obtain the effect of the present invention and are preferred as a modification functional group. Though a carboxyl group is a functional group having an electron attractive property, the studies conducted by the present inventors have clarified that an occurrence of NV (−) is enhanced even when a carboxyl group modifies a nanodiamond particle.

<<Surface Modification Treatment>>

In general, a wide variety of functional groups are present at a surface of a nanodiamond particle. Presence, for example, of an alkyl group, a carboxyl group, a ketone group, a hydroxyl group, a vinyl group, and a lactone group is known as such a functional group.

The nanodiamond particle in the present embodiment can be manufactured by performing treatment for selectively enhancing a ratio of modification with one or more types of functional groups containing a heteroatom, among such functional groups.

Here, the functional group containing a heteroatom is preferably one or more types of functional groups selected from the group consisting of a hydroxyl group, a hydroxyalkyl group, and a carboxyl group.

For example, a method of subjecting a functional group present at a surface of a nanodiamond particle to reduction treatment and/or oxidation treatment can suitably be employed as the treatment as above.

Here, when the treatment above is the reduction treatment, a ratio of modification of the surface of the nanodiamond particle with a hydroxyl group and/or a hydroxyalkyl group (at least any of a hydroxyl group and a hydroxyalkyl group) can selectively be enhanced. Any conventionally known reduction reaction can be adopted as a method of reduction treatment. Reduction treatment may be performed by using, for example, a borane-tetrahydrofuran solution mixture, lithium aluminum hydride, sodium borohydride, or a Fenton's reagent as a reduction agent.

The treatment above may be oxidation treatment. In the case of oxidation treatment, a ratio of modification of the surface of the nanodiamond particle with a carboxyl group can selectively be enhanced. Any conventionally known oxidation reaction can be adopted as a method of oxidation treatment. Oxidation treatment may be performed by using, for example, a solution mixture of concentrated sulfuric acid and concentrated nitric acid, a Piranha solution, sulfuric acid, nitric acid, or a perchloric acid solution mixture as an oxidizer.

<<Identification of Surface-Modifying Functional Group>>

Identification of a functional group present at a surface of a nanodiamond particle is preferably made after surface modification treatment as above. Identification of a functional group can be made, for example, by measuring an infrared spectroscopic spectrum (hereinafter also denoted as an "IR spectrum"). For example, an IR spectrum can be measured with a nanodiamond particle being formed into a pellet with a conventionally known pellet method.

<<Evaluation of ODMR Intensity>>

ODMR intensity can be evaluated by measuring an amount of emission of fluorescence by applying high-frequency magnetic field generating ESR while emitting excitation light to a nanodiamond particle and calculating ODMR intensity based on the equation (I).

<<Evaluation of Occurrence of NV (−)>>

An occurrence of NV (−) can also be evaluated by finding ODMR intensity for each individual particle of a certain number of nanodiamond particles treated under the same conditions and calculating an arithmetic mean thereof. Here, in order to obtain a reliable result, the certain number above is preferably set, for example, to approximately 50 to 200.

<<Others>>

The nanodiamond particle in the present embodiment has high ODMR intensity as above. Here, from a point of view of further enhancement of ODMR intensity, the nanodiamond particle preferably contains no rare earth metal (such as ytterbium (Yb), erbium (Er), or thulium (Tm)) in the inside of a crystal, because, when a rare earth metal is introduced into the crystal, strain is caused in a diamond crystal lattice and ODMR intensity may lower. The diamond crystal preferably contains no magnetic element (such as manganese (Mn), iron (Fe), nickel (Ni), cobalt (Co), or copper (Cu)) either, because magnetic field produced by these magnetic elements may adversely affect measurement of ODMR intensity.

Carbon occurring in nature can be employed as carbon forming a diamond crystal in the present embodiment, without being particularly limited. For example, there are $^{12}C$ and $^{13}C$ available as stable isotopes of naturally occurring carbon, however, a ratio of occurrence thereof in a diamond crystal is not particularly limited either.

Second Embodiment

Such a nanodiamond particle in the present embodiment is manufactured with a manufacturing method as below. In other words, the nanodiamond particle manufactured with the manufacturing method as below exhibits characteristics as above. Therefore, the nanodiamond particle in the present embodiment has an excellent effect to exhibit extremely high ODMR intensity. A method of manufacturing a nanodiamond particle in the present embodiment will be described below.

<Method of Manufacturing Nanodiamond Particle Including NV Center Having ODMR Intensity Enhanced>

Figure 12:
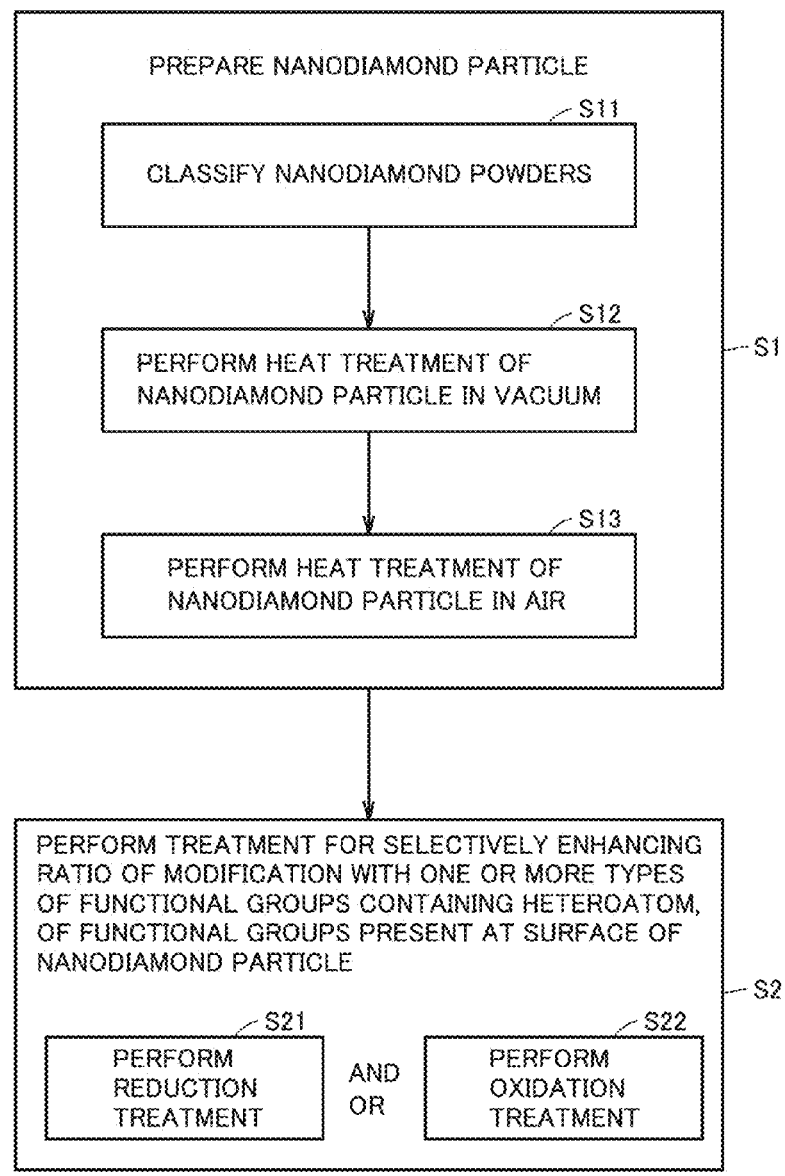
FIG. 12 is a flowchart showing a method of manufacturing a nanodiamond particle including an NV center having ODMR intensity enhanced according to an embodiment of the present invention.

FIG. 12 shows a flowchart of the method of manufacturing a nanodiamond particle in the present embodiment. The manufacturing method includes a step S1 of preparing a nanodiamond particle and a step S2 of performing treatment for selectively enhancing a ratio of modification with one or more types of functional groups containing a heteroatom, of functional groups present at a surface of the nanodiamond particle. Each step will be described below.

<<Step S1 of Preparing Nanodiamond Particle>>

Initially, in step S1, a step S11 of classifying nanodiamond powders, a step S12 of subjecting nanodiamond particles to heat treatment in vacuum, and a step S13 of subjecting the nanodiamond particles to heat treatment in air are performed. By performing step S11, the nanodiamond particles are adjusted to have particle size distribution suitable for use in a biological system, and by performing step S12, an NV center is formed in the inside of the nanodiamond particle. By further performing step S13, a graphite layer at the surface of the nanodiamond particle is oxidized, and thus the nanodiamond particle including the NV center exhibiting fluorescence can be manufactured. When diamond powders obtained with the detonation method are employed as described previously, the step of classification can be omitted.

<<Step S2 of Performing Treatment for Selectively Enhancing Ratio of Modification with Functional Group Containing Heteroatom>>

Then, in step S2, by subjecting the nanodiamond particles obtained in step S1 above to a step S21 of performing reduction treatment and/or a step S22 of performing oxidation treatment as the step of performing treatment for selectively enhancing a ratio of modification with one or more types of functional groups containing a heteroatom, of the functional groups present at the surface of the particle, the nanodiamond particle including the NV center having ODMR intensity enhanced can be manufactured.

The method of manufacturing a nanodiamond particle in the present embodiment may include other steps so long as it includes step S1 above (step S11 to step S13) and step S2 (at least any of step S21 and step S22), and an effect of the present invention is exhibited so long as step S1 and step S2 are included.

Here, other steps can include, for example, a step of drying nanodiamond particles after step S2. When the nanodiamond particles having the surface modified are dried, freeze-drying is desirably performed. This is because, with freeze-drying, nanodiamond particles can be prevented from aggregating and forming a cluster. In contrast, for example, drying under a reduced pressure will lead to aggregation of nanodiamond particles and formation of a cluster, which is not preferred.

For use in analysis of a structure of a biomolecule, the nanodiamond particle in the present embodiment preferably has a small particle size as described previously. The nanodiamond particle in the present embodiment is particularly preferably a single particle rather than an aggregate, for the following reason.

As will be described later, in a method of analyzing a structure of a protein in the present embodiment, a rotational motion of an N-V axis is tracked by tracking an angle formed between an N-V axis vector in a nanodiamond particle and a vector in external magnetic field (static magnetic field). Here, an NV center in a diamond crystal has four N-V axes. Therefore, when an aggregate of nanodiamond particles is employed as a fluorescent molecular probe, a plurality of nanodiamond particles in the aggregate are present at a small distance from one another in various directions (angles) and the plurality of N-V axes are also variously oriented. Thus, resolution of an ODMR signal lowers. Therefore, the nanodiamond particle in the present embodiment is preferably a single particle and a process in which no aggregate is produced is preferably adopted as the method of manufacturing the same.

Third Embodiment

A fluorescent molecular probe representing a specific application of a nanodiamond particle in the present embodiment described above to biometric measurement will be described below.

<Fluorescent Molecular Probe>

The fluorescent molecular probe in the present embodiment is obtained by chemically modifying a nanodiamond particle including an NV center having ODMR intensity enhanced.

Here, in consideration of measurement in a biological system, a nanodiamond particle having a particle size from 1 to 10 nm among the nanodiamond particles in the present embodiment is preferred as the nanodiamond particle to be used for the fluorescent molecular probe.

In order to secure a sufficient S/N ratio and obtain high time resolution in ODMR measurement, of the nanodiamond particles in the present embodiment, nanodiamond particles having ODMR intensity not lower than 0.02 are preferred, nanodiamond particles having ODMR intensity not lower than 0.05 are more preferred, and nanodiamond particles having ODMR intensity not lower than 0.10 are particularly preferred.

<<Chemical Modification>>

Here, chemical modification refers to chemical bonding to nanodiamond, of a molecular chain specifically bonding to a target protein. The molecular chain may directly be bonded to a carbon atom forming a diamond crystal or may be bonded to a functional group on a surface of a nanodiamond particle. The molecular chain is preferably selected as appropriate in accordance with a target protein. For example, when a metabotropic glutamate receptor which will be described later is designated as a target, ampicilin (which may hereinafter also be abbreviated as "Amp") can be employed.

<<Method of Inhibiting Non-Specific Adsorption>>

Chemical modification above preferably includes a molecular chain inhibiting non-specific adsorption to a biopolymer other than a target protein. One example of such a molecular chain can include, for example, hyperbranched polyglycerol (HPG). As chemical modification includes a molecular chain inhibiting non-specific adsorption, a target protein can highly selectively be labeled.

Figure 16:
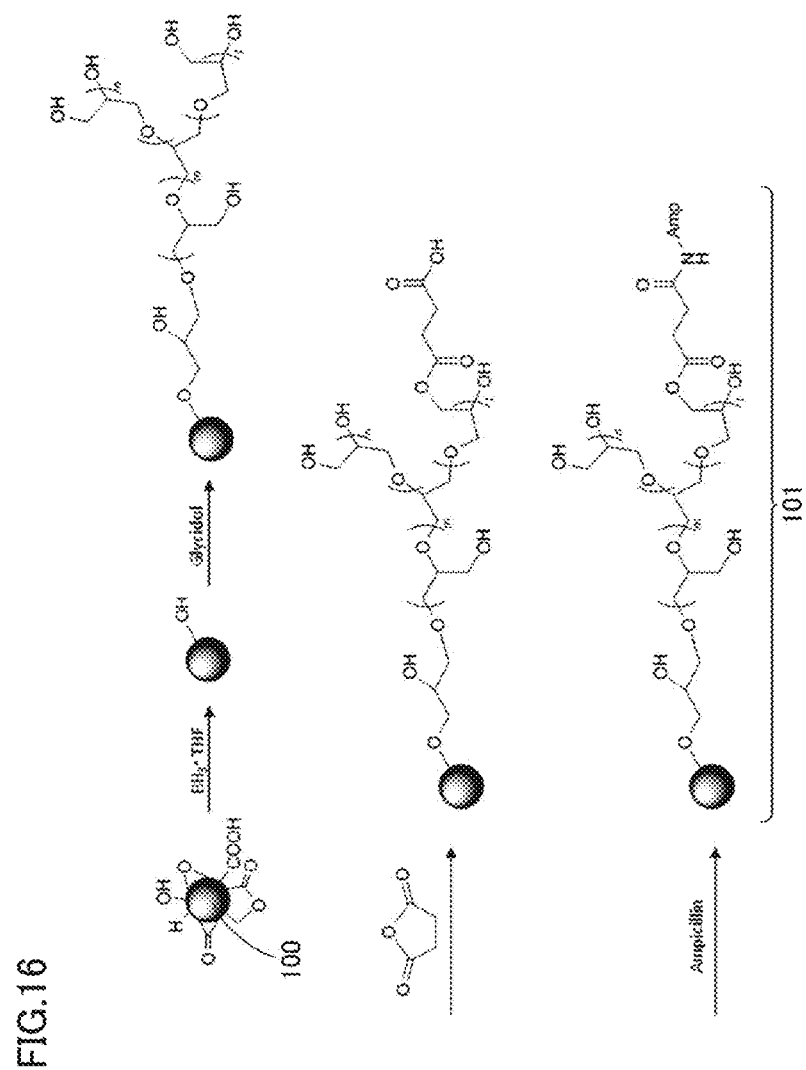
FIG. 16 is a diagram showing one example of a scheme for synthesizing a fluorescent molecular probe according to an embodiment of the present invention.

FIG. 16 shows one example of a scheme for synthesizing the fluorescent molecular probe in the present embodiment. As shown in FIG. 16, the fluorescent molecular probe in the present embodiment can be synthesized in accordance with a procedure in (i) to (iii) below. Namely, a fluorescent molecular probe 101 in the present embodiment can be synthesized by (i) enhancing ODMR intensity by modifying a surface of a nanodiamond particle 100, for example, with a hydroxyl group, (ii) bonding a molecular chain inhibiting non-specific adsorption to the hydroxyl group, and (iii) further making modification with a molecular chain specifically bonding to a target protein. FIG. 16 shows an example in which HPG is adopted as a molecular chain inhibiting non-specific adsorption and Amp is adopted as a molecular chain specifically bonding to a target protein.

EXPERIMENTAL EXAMPLES

Here, a specific example in which non-specific adsorption was successfully inhibited will be described with reference to experimental examples. Initially, (i) ODMR intensity was augmented by modifying a nanodiamond particle with a hydroxyl group. Then, (ii) the surface-modified nanodiamond particle was obtained by bonding a molecular chain shown in [a] to [c] below to this nanodiamond particle (that is, with surface-modification with the molecular chain).

[a] carboxyl group
[b] polyethylene glycol (PEG)
[c] HPG

In the description of the experimental example below, in accordance with the reference characters [a] to [c] above, a nanodiamond particle of which surface was modified with a carboxyl group is denoted as "ND [a]", a nanodiamond particle of which surface was modified with PEG is denoted as "ND [b]", and a nanodiamond particle of which surface was modified with HPG is denoted as "ND [c]".

Experimental Example 1

In Experimental Example 1, non-specific adsorption of a nanodiamond particle to a surface of a cell was evaluated.

NDs [a] to [c] obtained above were added to A431 (a human cell line derived from epidermoid carcinoma) cultured in a Dulbecco's Modified Eagle's Medium (DMEM) such that a concentration thereof was set to 1 mg/ml, and test cell lines [a] to [c] were thus prepared. Here, for example, the test cell line [a] refers to a test cell line to which ND [a] was added such that a concentration thereof was set to 1 mg/ml.

Here, as a comparative experimental example, a specimen obtained by adding ND [c] such that a concentration thereof was set to 10 mg/ml (a test cell line [d]) was also fabricated.

Figure 17:
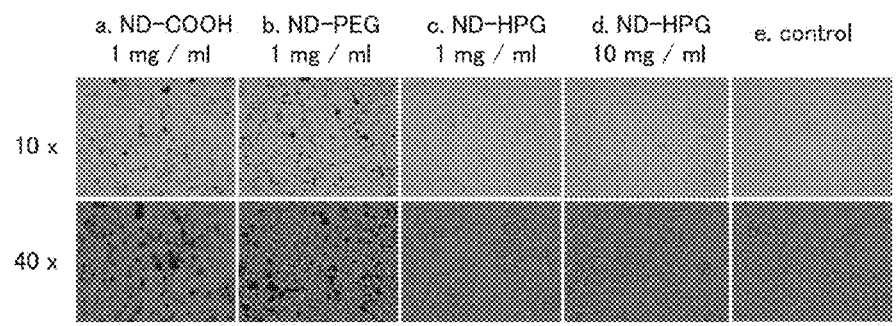
FIG. 17 is a diagram showing one example of a result of observation of a cell line to which a nanodiamond particle has been added.

Each test cell line was cultured for 2 hours and thereafter washed with physiological saline. Then, the nanodiamond particle adsorbed onto the cell included in each test cell line was observed with a bright-field microscope to check whether or not there is non-specific adsorption of the nanodiamond particle to a cell membrane. FIG. 17 shows a result thereof.

FIG. 17 shows an image of an observation field of view resulting from observation of each test cell line at a magnification of 10 and an image of an observation field of view resulting from observation of each test cell line at a magnification of 40, with the use of a bright-field microscope. In FIG. 17, "a. ND-COOH" represents the test cell line [a], "b. ND-PEG" represents the test cell line [b], "c. ND-HPG" represents the test cell line [c], and "d. ND-HPG" represents the test cell line [d]. In addition, "e. control" represents a control cell, that is, a cell line to which no nanodiamond particle was added.

As shown in FIG. 17, black points are present in the field of view for "a. ND-COOH" and "b. ND-PEG", and it can be seen that non-specific adsorption of the nanodiamond particle to the cell membrane occurred. In contrast, no such non-specific adsorption was observed for "c. ND-HPG" and "d. ND-HPG", and substantially no difference from "e. control" (the control cell) was observed. Namely, it was confirmed that non-specific adsorption of the nanodiamond particle to the surface of the cell could be inhibited by modifying the surface of the nanodiamond particle with HPG.

Experimental Example 2

In Experimental Example 2, non-specific adsorption of a protein to a nanodiamond particle was evaluated.

Initially, NDs [a] to [c] above were added to a lysozyme aqueous solution such that a concentration thereof was set to 2 mg/ml and test aqueous solutions [a] to [c] were thus prepared. Here, for example, the test aqueous solution [a] refers to a lysozyme aqueous solution to which ND[a] was added such that a concentration thereof was set to 2 mg/ml.

Figure 18:
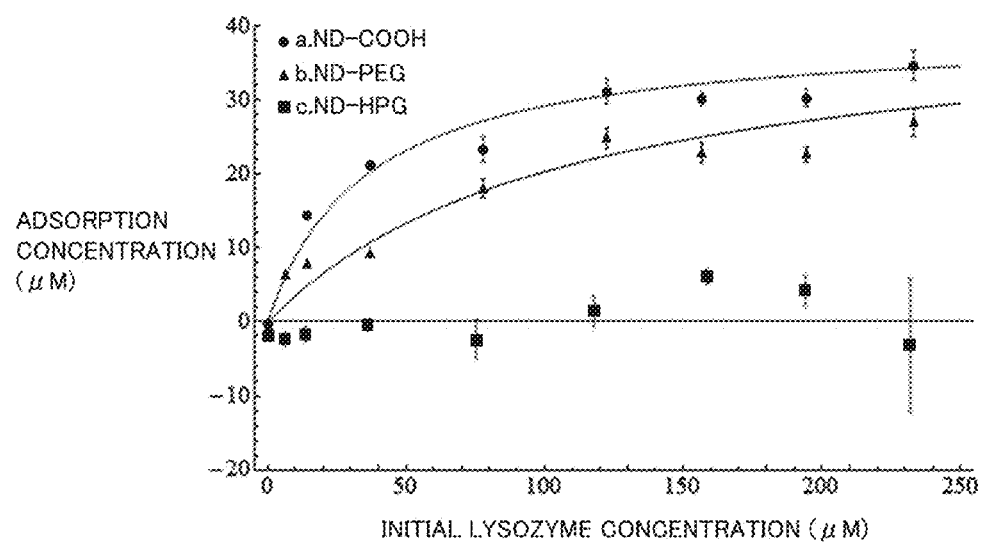
FIG. 18 is a graph showing one example of relation between a concentration of a protein in an aqueous solution and a concentration of a protein adsorbed onto a nanodiamond particle.

Then, an amount of protein (lysozyme) which was adsorbed to a surface of a nanodiamond particle in each aqueous solution was calculated by measuring absorbance at a wavelength of 280 nm. FIG. 18 shows a result thereof.

FIG. 18 is a graph showing relation between a concentration of lysozyme present in an aqueous solution and a concentration of lysozyme which was non-specifically adsorbed onto a surface of a nanodiamond particle in Experimental Example 2. In FIG. 18, the abscissa represents an initial lysozyme concentration before addition of a nanodiamond particle and the ordinate represents a concentration of lysozyme which was adsorbed onto the surface of the nanodiamond particle. In FIG. 18, a marker in a circular shape represents a result of ND [a], a marker in a triangular shape represents a result of ND [b], and a marker in a quadrangular shape represents a result of ND [c]. Measurement was conducted a plurality of times for each concentration and a standard deviation of results is indicated by an error bar. A curve in FIG. 18 is provided for assistance in easy representation of results.

As is clear from FIG. 18, tendency of ND [a] and ND [b] of more non-specific adsorption of lysozyme to a surface of a nanodiamond particle with increase in initial lysozyme concentration was observed. In contrast, for ND [c] (the nanodiamond particle of which surface was modified with HPG), even with increase in initial lysozyme concentration, an amount of lysozyme which was adsorbed onto the surface of the nanodiamond particle stayed around zero (0). Namely, it was confirmed that non-specific adsorption to a nanodiamond particle, of a protein (in this example, lysozyme) other than a target protein could be inhibited by modifying a surface of the nanodiamond particle with HPG.

<<Target Protein>>

A target protein to be observed in the present embodiment can be exemplified by a metabotropic glutamate receptor (hereinafter also denoted as "mGluR"). It has been expected based on findings in structural biology so far that mGluR changes a conformation of a dimer in transmission of a signal within a cell. Actual observation of this structural change has not so far been reported. According to the fluorescent molecular probe in the present embodiment and the method of analyzing a structure of a protein in the present embodiment which will be described later, structural change above is highly likely to be observed for the first time.

Fourth Embodiment

A method of analyzing a structure of a protein in the present embodiment with the use of the fluorescent molecular probe above will be described below.

<Method of Analyzing Structure of Protein>

Figure 21:
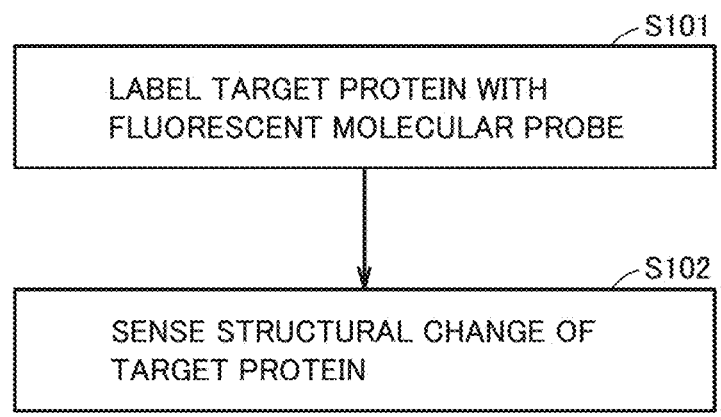
FIG. 21 is a flowchart showing overview of a method of analyzing a structure of a protein according to an embodiment of the present invention.

FIG. 21 is a flowchart showing overview of the method of analyzing a structure of a protein in the present embodiment. As shown in FIG. 21, the method of analyzing a structure of a protein in the present embodiment is a method of analyzing a structure of a protein by sensing change in structure of a target protein by emitting excitation light and applying high-frequency magnetic field from 1 to 5 GHz to a target protein labeled with the fluorescent molecular probe in the present embodiment and sensing a peak magnetic field frequency at which a fluorescence spectrum decreases. Namely, the method of analyzing a structure of a protein in the present embodiment includes a step S101 of labeling a target protein with a fluorescent molecular probe and a step S102 of sensing structural change of the target protein by emitting excitation light and applying high-frequency magnetic field from 1 to 5 GHz to the labeled target protein and sensing a peak magnetic field frequency at which an amount of emission of fluorescence decreases.

Figure 9:
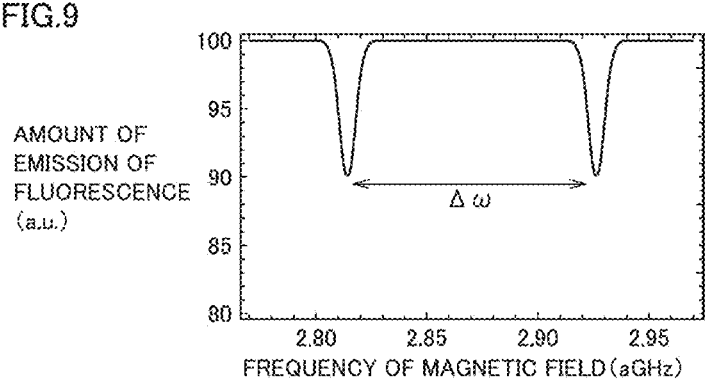
FIG. 9 is a diagram showing one example of an ODMR spectrum in a method of analyzing a structure of a protein according to an embodiment of the present invention.

As shown in FIG. 9, the peak magnetic field frequency splits under static external magnetic field and a rotational motion of an NV center included in the fluorescent molecular probe can be sensed based on magnitude of splitting, so that structural change of a target protein can be tracked.

<<Step S101 of Labeling Target Protein with Fluorescent Molecular Probe>>

In order to label a target protein with a fluorescent molecular probe, initially, a target protein and a protein serving as a tag (hereinafter also denoted as a "tag-protein") are fused with each other. For example, when mGluR exemplified above is designated as a target, a mutant of β-lactamase derived from bacteria (hereinafter also denoted as a "BL tag") can be adopted as a tag-protein.

For example, by transfecting DNA having a base sequence of mGluR and the BL tag encoded into a HeLa cell with lipofection, a protein in which mGluR and the BL tag have been fused can be expressed in the HeLa cell.

Here, a nanodiamond particle obtained by chemically modifying Amp specifically reacting with the BL tag can be employed as the fluorescent molecular probe. By bonding the BL tag and the nanodiamond particle to each other with Amp, mGluR can be labeled with the nanodiamond particle.

<<Step S102 of Sensing Structural Change of Target Protein>>

As above, a structure of a labeled target protein can be analyzed by detecting a rotational motion of an N-V axis within a diamond crystal included in the fluorescent molecular probe, through ODMR measurement.

(N-V Axis)

Here, the N-V axis refers to a straight axis connecting a nitrogen atom (N) and an adjacent vacancy (V) to each other in an NV center within a diamond crystal. The NV center has a magnetic moment $\mu_{NV}$ on the N-V axis.

(Detection of Rotational Motion)

Similarly to the ODMR spectrum shown in FIG. 9, an ODMR signal of NV (−) included in a nanodiamond particle splits into two under static external magnetic field owing to the Zeeman effect. The two split ODMR signals are symmetric with respect to approximately 2.87 GHz, which indicates that a degenerated energy level of Mz=±1 splits into two energy levels of Mz=+1 and Mz=−1 owing to the Zeeman effect. Here, with the splitting of the ODMR signal being denoted as Δω, Δω varies in correspondence with an angle θ formed between the N-V axis and static magnetic field.

Therefore, angle θ formed between the N-V axis and static magnetic field can be calculated in an equation (II)

below, for example, based on splitting $\Delta\omega$ of the peak in the ODMR spectrum shown in FIG. 9.

$$\theta = \cos^{-1}(h\Delta\omega/\mu_{NV}B_0) \quad \text{(II)}$$

The equation (II) represents an inner product of an N-V axis vector and a vector in the static magnetic field, where θ represents an angle formed between the N-V axis and the static magnetic field, h represents a reduced Planck constant, $\Delta\omega$ represents splitting of the peak of the ODMR spectrum, $\mu_{NV}$ represents a magnetic moment of the NV center, and $B_0$ represents intensity of the static magnetic field.

Splitting $\Delta\omega$ of the peak is calculated as $\Delta\omega=\omega_1-\omega_2$, where $\omega_1$ and $\omega_2$ (with $\omega_1$ and $\omega_2$ satisfying relation of $\omega_1>\omega_2$) represent frequencies at respective peak tops of downward peaks of two amounts of emission of fluorescence in the ODMR spectrum.

Therefore, by tracking change over time in $\Delta\omega$, a rotational motion of the N-V axis can be tracked. Thus, when a specific site of a protein is labeled, for example, with a fluorescent molecular probe including a nanodiamond particle including NV (−), a rotational motion of that site can be tracked and hence structural change of the protein can be tracked.

For example, when mGluR is labeled with the fluorescent molecular probe in the present embodiment as described above, conformation of a dimer of mGluR can be measured in real time.

<<Analysis Apparatus>>

Figure 13:
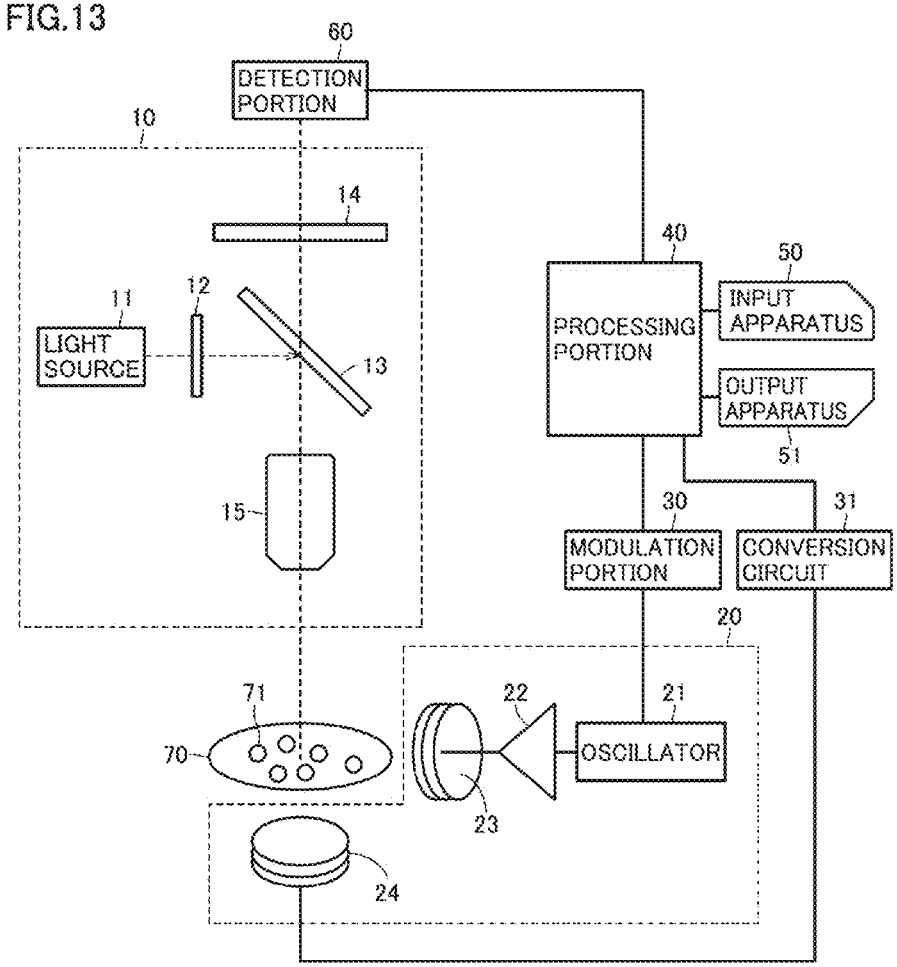
FIG. 13 is a schematic conceptual diagram showing an analysis apparatus involved with a method of analyzing a structure of a protein in an embodiment of the present invention.

Analysis of a structure of a protein as described above can be made with an analysis apparatus as below. FIG. 13 is a schematic conceptual view showing one example of an analysis apparatus involved with the method of analyzing a structure of a protein in the present embodiment. This analysis apparatus is broadly divided, for each function, into an optical detection portion, a magnetic resonance portion, and a console portion.

The optical detection portion is implemented by a fluorescence microscope capable of single-molecule fluorescence measurement. For example, as shown in FIG. 13, the optical detection portion can be implemented by an optical microscope 10 and a detection portion 60 capable of detecting fluorescence. Here, an avalanche photodiode or an electron multiplication cooled CCD camera which has ultra-high sensitivity and high quantitative capability as a fluorescence detector is desirably employed as detection portion 60.

The magnetic resonance portion (a high-frequency magnetic field generation portion 20) is mainly constituted of an electromagnet (not shown), an oscillator 21, a high-frequency coil 23, and a static magnetic field coil 24. An electromagnet not higher than 50 gausses may be applicable, however, the electromagnet is desirably capable of controlling a magnetic direction. Oscillator 21 should be a high-frequency oscillator capable of controlling oscillation at a nanosecond level. High-frequency coil 23 serves to produce ESR in a sample, and static magnetic field coil 24 serves to change static magnetic field in an arbitrary direction.

The console portion is constituted of a workstation, a conversion circuit 31, and a modulation portion 30. A workstation having, for example, a processing portion 40, an input apparatus 50, and an output apparatus 51 can be used as the workstation. Conversion circuit 31 is implemented specifically by a digital to analog converter (DAC), and modulation portion 30 is implemented specifically by a pulse/delay generator.

In this analysis apparatus, the optical detection portion and the magnetic resonance portion should be in synchronization with each other at accuracy from picosecond to nanosecond with the use of the DAC and the pulse/delay generator. The workstation is responsible for setting of the optical detection portion and the magnetic resonance portion and control of the DAC and the pulse/delay generator. The workstation serves to take in a fluorescence signal detected by the optical detection portion in real time, control the apparatus recursively, and analyze measurement data.

Though a method of analyzing measurement data is not particularly restricted, for example, a method of analyzing a direction based on fitting between a high-frequency domain spectrum simulated from a spin Hamiltonian energy eigenvalue and an actually obtained measurement result or a method of analyzing a frequency of a time domain signal of ODMR intensity can be employed.

EXAMPLES

Though the present invention will be described below in further detail with reference to Examples, the present invention is not limited thereto.

Example 1

In Example 1, Example 2, and Comparative Example 1 shown below, ODMR intensity of nanodiamond powders obtained with the HPHT method was evaluated.

<Manufacturing of Nanodiamond Particle Including NV Center>

<<Step S1 of Preparing Nanodiamond Particle>>

Initially, nanodiamond powders obtained with the HPHT method (product name "Micron+MDA, 0-0.10 μm" manufactured by Element Six) were prepared as a starting source material.

(Step S11 of Classification)

Diamond particles were classified by dispersing these nanodiamond powders in water and centrifuging the nanodiamond powders for 20 minutes at 15000 rpm. An average particle size of the nanodiamond particles thus obtained was found with a dynamic light scattering method with the use of a laser diffraction and scattering particle size analysis instrument (product name "Microtrac II" manufactured by Nikkiso Co., Ltd.). The average particle size was 27.3 nm and a standard deviation of particle size distribution was 7.3 nm.

(Step S12 of Performing Heat Treatment in Vacuum)

Then, the nanodiamond particles obtained through a classification process were subjected to heat treatment in vacuum at 800° C. and a NV center was formed in a diamond crystal.

(Step S13 of Performing Heat Treatment in Air)

Then, a surface was oxidized through heat treatment in air at 550° C.

<<Step S2 of Performing Treatment for Selectively Enhancing Ratio of Modification with Functional Group Containing Heteroatom>>

(Step S21 of Performing Reduction Treatment)

Ten milligrams of nanodiamond particles obtained as above and 300 μl of borane-tetrahydrofuran complex (product name, manufactured by ALDRICH) were introduced in a reactor made of glass, 5 ml of tetrahydrofuran was further added thereto, and the mixture was refluxed at 70° C. in an atmosphere of argon and stirred for 24 hours. Then, a supernatant was removed, and the resultant product was washed with acetone and ultrapure water and thereafter dried. Thus, a nanodiamond particle including an NV center having ODMR intensity enhanced was obtained.

Example 2

A nanodiamond particle including an NV center having ODMR intensity enhanced was obtained as in Example 1, except that reduction treatment was not performed but oxidation treatment below was performed in manufacturing of a nanodiamond particle including an NV center in Example 1.

<<Step S22 of Performing Oxidation Treatment>>

Eleven milligrams of nanodiamond powders subjected to heat treatment in air and 5 ml of a solution in which concentrated sulfuric acid and concentrated nitric acid had been mixed at a volume ratio of 9:1 were introduced in a reactor made of glass and stirred for 72 hours at 75° C. Then, a nanodiamond particle was obtained by removing a supernatant and washing the resultant product with ultrapure water followed by drying.

Comparative Example 1

A nanodiamond particle including an NV center was obtained as in Example 1 except that reduction treatment was not performed in manufacturing of a nanodiamond particle including an NV center in Example 1.

<Evaluation of Nanodiamond Particle Including NV Center>

<<Identification of Modification Functional Group>>

Identification of a functional group present at a surface of the nanodiamond particles in Example 1, Example 2, and Comparative Example 1 obtained as above was made as below (an IR spectrum was measured). Here, in Example 1 or Example 2, nanodiamond particles subjected to reduction treatment or oxidation treatment were adopted as samples. Regarding the nanodiamond particle in Comparative Example 1, the nanodiamond particle subjected to heat treatment in vacuum and yet to be subjected to heat treatment in air was adopted as a sample. This is because accuracy in measurement lowers due to an impurity caused in oxidation of graphite when IR is measured after heat treatment in air.

Figure 10:
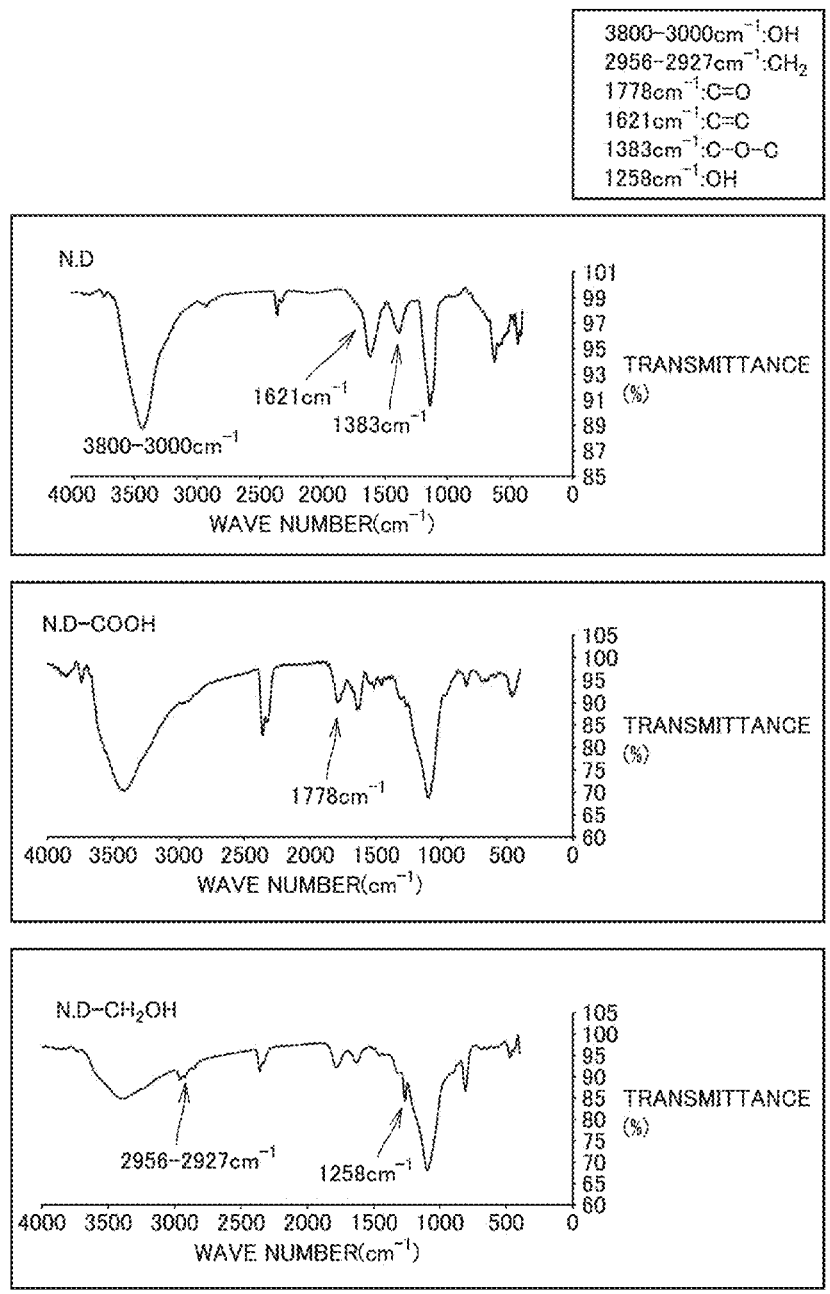
FIG. 10 is a diagram showing one example of an IR spectrum of a nanodiamond particle according to an embodiment of the present invention.

Initially, powders made of a trace amount of nanodiamond particles were added to and mixed with powders of potassium bromide, to thereby form uniform powders. Thereafter, the mixed powders were introduced in a mold and pressed, to thereby prepare a measurement sample in a disc shape. Then, an IR spectrum of each measurement sample was measured with a Fourier transform infrared spectrometer (model number "FT/IR-4200" manufactured by JASCO Corporation). FIG. 10 shows results.

In FIG. 10, "N.D-CH$_2$OH" represents an IR spectrum of the nanodiamond particle in Example 1, "N.D-COOH" represents an IR spectrum of the nanodiamond particle in Example 2, and "N.D" represents an IR spectrum of the nanodiamond particle in Comparative Example 1.

As shown in FIG. 10, peaks derived from various functional groups such as an alkyl group, a ketone group, an ether group, a hydroxyl group, a vinyl group, and a lactone group were observed for the nanodiamond particle in Comparative Example 1. In contrast, for the nanodiamond particle in Example 1 (reduction treatment), peaks derived from a hydroxyalkyl group (1258 cm$^{-1}$, 2956-2927 cm$^{-1}$) could be observed and peaks derived from other functional groups were relatively less than in Comparative Example 1 (untreated). For the nanodiamond particle in Example 2 (oxidation treatment), a peak derived from a carboxyl group (1778 cm$^{-1}$) could clearly be observed and peaks derived from other functional groups were relatively less than in Comparative Example 1 (untreated). Namely, it could be confirmed that the nanodiamond particle in Example 1 had the surface modified with a hydroxyl group and/or a hydroxyalkyl group, and the nanodiamond particle in Example 2 had the surface modified with a carboxyl group.

<<Evaluation of ODMR Intensity and NV (−) Occurrence>>

ODMR intensity in Example 1, Example 2, and Comparative Example 1 was evaluated as below.

Figure 11:
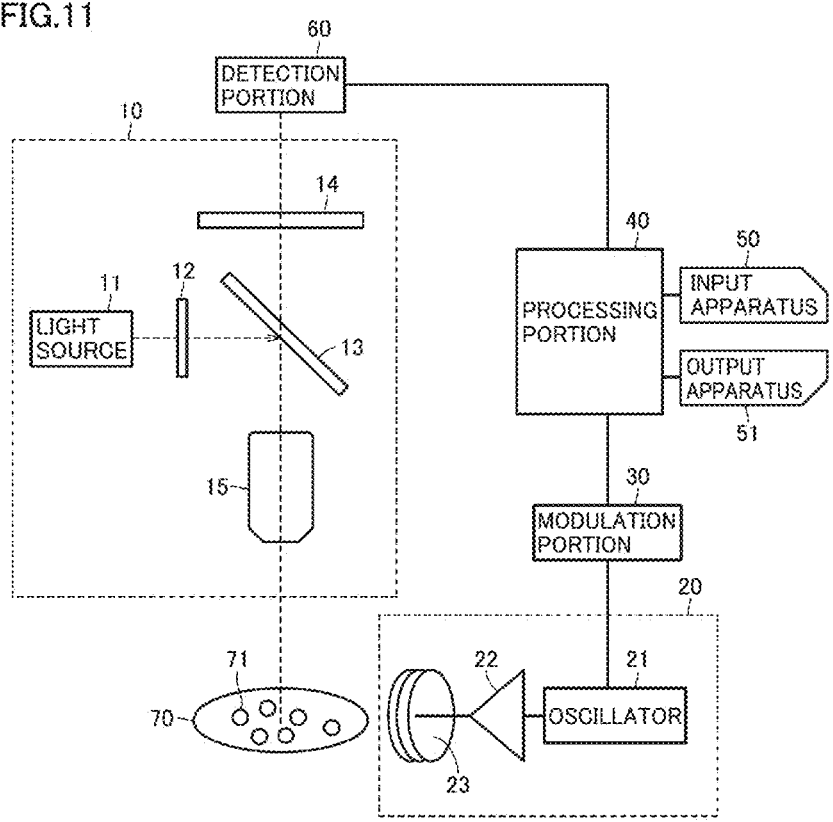
FIG. 11 is a schematic conceptual diagram showing one example of a fluorescence microscope apparatus used for evaluating ODMR intensity according to an embodiment of the present invention.

Initially, a fluorescent microscope apparatus used for evaluation of ODMR intensity will be described with reference to FIG. 11. The fluorescent microscope apparatus includes optical microscope 10, high-frequency magnetic field generation portion 20, modulation portion 30, processing portion 40, input apparatus 50, and output apparatus 51. Optical microscope 10 includes a light source 11, an excitation filter 12, a dichroic mirror 13, a band filter 14, and an objective 15. High-frequency magnetic field generation portion 20 includes oscillator 21, an amplification portion 22, and high-frequency coil 23. This apparatus provided with conversion circuit 31 and static magnetic field coil 24 for changing static magnetic field in an arbitrary direction is the same as the analysis apparatus used for analysis of a structure of a protein described previously (see FIG. 13).

Light emitted from light source 11 passes through excitation filter 12 and becomes excitation light. The excitation light is reflected by dichroic mirror 13 and emitted to a sample stage 70 through objective 15. Fluorescence generated from a sample 71 excited by the excitation light is not reflected by dichroic mirror 13 but travels in straight lines toward detection portion 60, at which an amount of emission of fluorescence is measured. Sample 71 is irradiated with high-frequency magnetic field from high-frequency magnetic field generation portion 20. As a result of irradiation with high-frequency magnetic field, ESR is generated in sample 71. By measuring change in amount of emission of fluorescence at that time with detection portion 60, processing portion 40 can calculate ODMR intensity in accordance with the equation (I) above.

Initially, on the sample stage of the fluorescence microscope apparatus described above, a powder sample made of the nanodiamond particles in Example 1 was suspended in water and applied to a glass slide. A bright spot resulting from emission of fluorescence of the nanodiamond particle was observed on a screen of output apparatus 51, by irradiating the sample with excitation light. Then, ODMR intensity was measured by applying high-frequency magnetic field to thereby decrease an amount of emission of fluorescence. Similar measurement was conducted for 100 particles.

Figure 14:
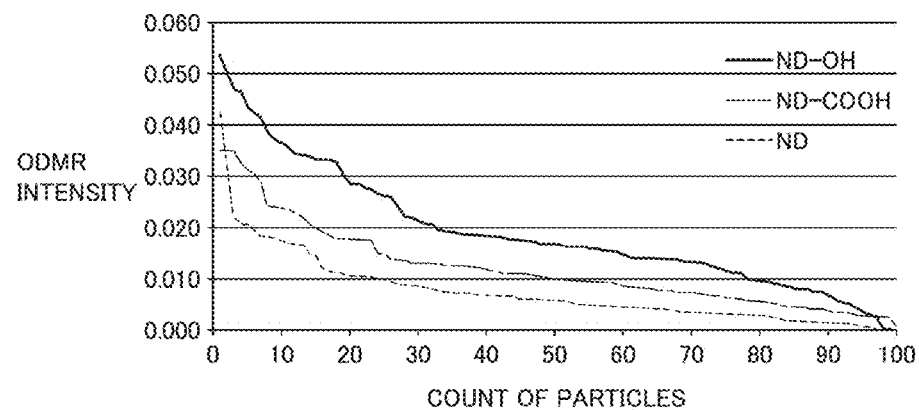
FIG. 14 is a graph showing an example of measurement of ODMR intensity of a nanodiamond particle according to an embodiment of the present invention.
Figure 15:
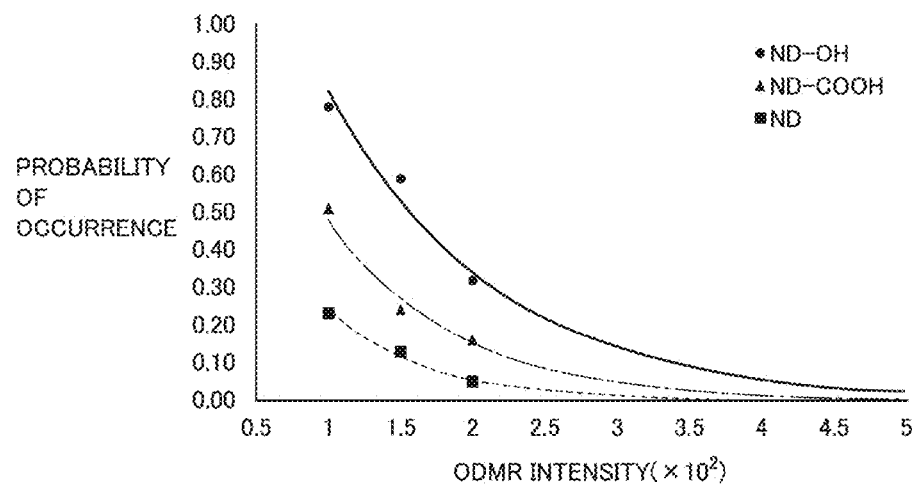
FIG. 15 is a graph showing an example of measurement of ODMR intensity of a nanodiamond particle according to an embodiment of the present invention.

ODMR intensities of 100 particles of the nanodiamond particles in Example 2 and Comparative Example 1 were also measured as above. Table 1 and FIGS. 14 and 15 show results.

TABLE 1

| | Surface Treatment | Modification Functional Group | Measurement Result | | | |
|---|---|---|---|---|---|---|
| | | | Cumulated Frequency of Particles Not Lower Than Each ODMR Intensity (Count in 100 Particles) | | | Arithmetic Mean |
| | | | ODMR Intensity Not Lower Than 0.01 | ODMR Intensity Not Lower Than 0.02 | ODMR Intensity Not Lower Than 0.05 | Value of ODMR Intensities of 100 Particles |
| Example 1 | Reduction Treatment | Hydroxyalkyl Group Hydroxyl Group | 77% | 32% | 2% | 0.0190 |
| Example 2 | Oxidation Treatment | Carboxyl Group | 49% | 14% | 0% | 0.0119 |
| Comparative Example 1 | Untreated | Various Types of Functional Groups Being Randomly Present | 23% | 3% | 0% | 0.0074 |

Numeric values shown in the field of the measurement result in Table 1 show a cumulated frequency (%) of particles among 100 particles, which have ODMR intensities equal to or higher than a certain value (0.01 or higher, 0.02 or higher, 0.05 or higher), and an arithmetic mean value of ODMR intensities of 100 particles.

FIG. 14 shows a graph showing a result of measurement of ODMR intensities of 100 particles and gives representation of results of ODMR intensities of particles in descending order. In FIG. 14, a solid line shows a result of Example 1, a chain dotted line shows a result of Example 2, and a dotted line shows a result of Comparative Example 1.

FIG. 15 shows a graph showing relation between ODMR intensity and a probability of occurrence of particles, and shows on the ordinate a probability of occurrence of particles having ODMR intensities equal to or higher than a numeric value for ODMR intensity shown on the abscissa. In FIG. 15, a circular mark and a solid line show a result of Example 1, a triangular mark and a chain dotted line show a result of Example 2, and a quadrangular mark and a dotted line show a result of Comparative Example 1. Numeric values on the abscissa in FIG. 15 are shown as being multiplied by 100.

As is clear from Table 1 and FIGS. 14 and 15, particles having high ODMR intensities were included in the nanodiamond particles more in Example 1 and Example 2 than in the nanodiamond particles in Comparative Example 1 which had not been treated. In particular, the nanodiamond particles in Example 1 included particles extremely high in ODMR intensity not lower than 0.05, which were not at all present in the nanodiamond particles in the comparative example.

It could be confirmed from the results above that an occurrence of NV (−) was increased and ODMR intensity was enhanced as nanodiamond particles in Examples included NV centers and had the surface modified with a functional group containing a heteroatom.

Example 3

In Example 3 and Comparative Example 2 shown below, ODMR intensity was evaluated using nanodiamond powders obtained with the detonation method.

Initially, nanodiamond powders obtained with the detonation method NanoAmando (trademark) Aqueous colloid (Dispersed 5 nm-Bucky Diamond)", manufactured by Nano-Carbon Research Institute, Ltd.) were prepared. Particles included in these nanodiamond powders were single particles, and particle sizes thereof range approximately from 4 nm to 5 nm.

Then, a nanodiamond particle according to Example 3 was obtained as in Example 1 except that step S11 of classifying nanodiamond powders was not performed.

Comparative Example 2

A nanodiamond particle according to Comparative Example 2 was obtained by subjecting the nanodiamond powders obtained with the detonation method above to heat treatment in vacuum at 800° C. and successively to heat treatment in air at 550° C. Namely, the nanodiamond particle according to Comparative Example 2 was obtained as in Example 3 except for not performing reduction treatment.

<<Evaluation of ODMR Intensity>>

ODMR intensities of the nanodiamond particles according to Example 3 and Comparative Example 2 obtained as above were evaluated with the use of the fluorescence microscope described previously (see FIG. 11). FIGS. 19A, 19B, 20A, and 20B and Table 2 show results.

TABLE 2

| | Surface Treatment | Modification Functional Group | Measurement Result | |
|---|---|---|---|---|
| | | | Amount of Emission of Fluorescence (R.L.U) | ODMR Intensity |
| Example 3 | Reduction Treatment | Hydroxyalkyl Group Hydroxyl Group | 6065 | 0.0237 |
| Comparative Example 2 | Untreated | Various Types of Functional Groups Being Randomly Present | 7194 | 0.0038 |

Figure 19A:
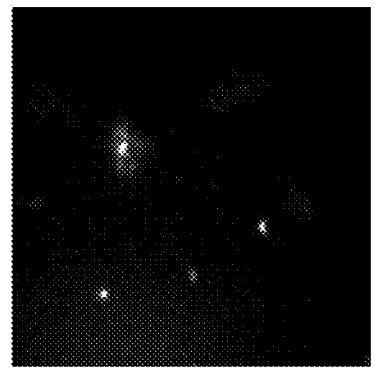
FIG. 19A is a diagram showing a fluorescence image of a nanodiamond particle according to an embodiment of the present invention.
Figure 19B:
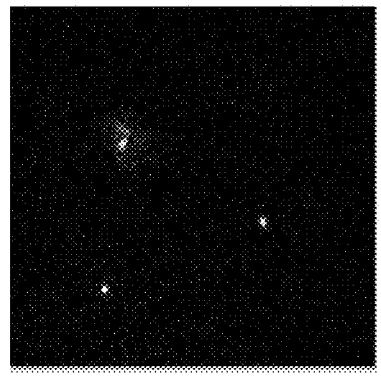
FIG. 19B is a diagram showing an ODMR image of a nanodiamond particle according to the embodiment of the present invention.
Figure 20A:
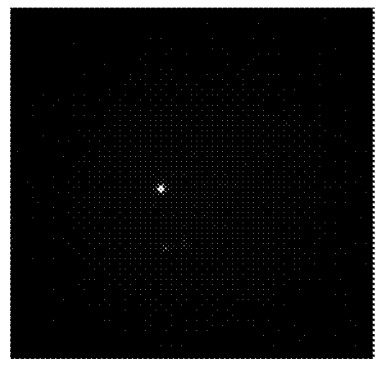
FIG. 20A is a diagram showing a fluorescence image of a conventional nanodiamond particle.
Figure 20B:
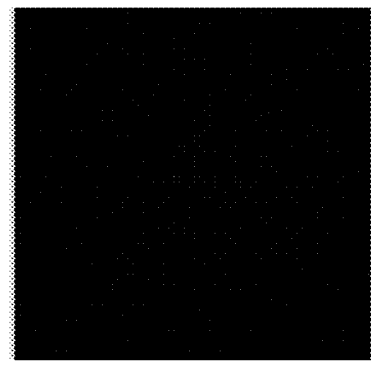
FIG. 20B is a diagram showing an ODMR image of the conventional nanodiamond particle.

Numeric values shown in fields of an amount of emission of fluorescence and ODMR intensity in Table 2 represent an amount of emission of fluorescence and ODMR intensity in images of a field of view shown in FIGS. 19A and 19B (Example 3) and FIGS. 20A and 20B (Comparative Example 2). An image shown in FIG. 19A shows an fluorescence image of the nanodiamond particle according to Example 3. As shown in FIG. 19A, three bright points resulting from emission of fluorescence of the nanodiamond particle can be observed in this image of the field of view. FIG. 19B shows an ODMR image in that field of view. Three bright points can clearly be observed in FIG. 19B, in correspondence with the bright points in 19A. Therefore, the nanodiamond particle according to Example 3 is ODMR active.

On the other hand, FIG. 20A shows a fluorescence image of the nanodiamond particle according to Comparative Example 2 and FIG. 20B shows an ODMR image of that nanodiamond particle. Though a bright point resulting from emission of fluorescence of the nanodiamond particle can be observed in FIG. 20A, no bright point can be observed in FIG. 20B. Therefore, the nanodiamond particle according to Comparative Example 2 is ODMR inactive.

From the results above, it could be confirmed that an occurrence of NV (−) was increased and ODMR intensity was enhanced by modifying the surface even of the diamond particle obtained with the detonation method with a functional group containing a heteroatom.

Though the embodiments and the examples of the present invention have been described above, combination of features in each embodiment and example described above as appropriate is also originally intended.

It should be understood that the embodiments and the examples disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST 1 carbon atom; 2 nitrogen atom; 3 vacancy; 4 unshared electron of nitrogen atom; 5 extra electron; 6 unpaired electron of carbon atom; 10 optical microscope; 11 light source; 12 excitation filter; 13 dichroic mirror; 14 band filter; 15 objective; 20 high-frequency magnetic field generation portion; 21 oscillator; 22 amplification portion; 23 high-frequency coil; 24 static magnetic field coil; 30 modulation portion; 31 conversion circuit; 40 processing portion; 50 input apparatus; 51 output apparatus; 60 detection portion; 70 sample stage; 71 sample; 100 nanodiamond particle; and 101 fluorescent molecular probe.

The invention claimed is:

1. A nanodiamond particle including a nitrogen atom and a vacancy (NV) center having optically-detected magnetic resonance (ODMR) intensity enhanced, of which surface is modified with an electron-donating functional group, wherein
said ODMR intensity represents a rate of decrease in an amount of fluorescence emission originating from excitation light when a high-frequency magnetic field from 1 to 5 GHz is applied, and
said rate of decrease in said amount of fluorescence emission is not less than 0.01.

2. The nanodiamond particle including an NV center having ODMR intensity enhanced according to claim 1, wherein said electron-donating functional group is at least any of a hydroxyl group and a hydroxyalkyl group.

3. The nanodiamond particle including an NV center having ODMR intensity enhanced according to claim 1, having an average particle size not smaller than 1 nm and not greater than 50 nm.

4. A powdery reagent formed from the nanodiamond particle including an NV center having ODMR intensity enhanced according to claim 1 or a reagent obtained by dispersing said nanodiamond particle in a liquid.

5. A fluorescent molecular probe obtained by chemically modifying the nanodiamond particle including an NV center having ODMR intensity enhanced according to claim 1, wherein said chemically modifying includes modifying said nanodiamond particle with a molecular chain that bonds to a target protein.

6. A powder reagent formed from the fluorescent molecular probe according to claim 5 or a reagent obtained by dispersing said fluorescent molecular probe in a liquid.

7. A method of analyzing a structure of a protein, comprising the steps of:
labeling said target protein with the fluorescent molecular probe according to claim 5; and
sensing structural change of said target protein by emitting excitation light and applying high-frequency magnetic field from 1 to 5 GHz to labeled said target protein and sensing a peak magnetic field frequency at which an amount of emission of fluorescence decreases.

8. The method of analyzing a structure of a protein according to claim 7, wherein
in said step of sensing, said peak magnetic field frequency splits under static external magnetic field, and
said step of sensing includes the step of sensing a rotational motion of an NV center included in said fluorescent molecular probe based on magnitude of splitting of said peak magnetic field frequency.

9. The fluorescent molecular probe according to claim 5, chemically modified with hyperbranched polyglycerol.

10. A method of manufacturing a nanodiamond particle including a nitrogen atom and a vacancy (NV) center having optically-detected magnetic resonance (ODMR) intensity enhanced, comprising the steps of:
preparing a nanodiamond particle; and
performing treatment for selectively enhancing a ratio of modification with one or more types of electron-donating functional groups among functional groups present at a surface of said nanodiamond particle, wherein
said ODMR intensity represents a rate of decrease in an amount of fluorescence emission originating from excitation light when a high-frequency magnetic field from 1 to 5 GHz is applied, and
said rate of decrease in said amount of fluorescence emission is not less than 0.01.

11. The method of manufacturing a nanodiamond particle including an NV center having ODMR intensity enhanced according to claim 10, wherein
said electron-donating functional group is at least any of a hydroxyl group and a hydroxyalkyl group and said performing treatment is a reduction treatment.

* * * * *